United States Patent [19]

Mander

[11] Patent Number: Plant 5,852

[45] Date of Patent: Jan. 13, 1987

[54] ROSE PLANT—CANADIAN WHITE STAR

[76] Inventor: George Mander, 2232 Gale Avenue, Coquitlam, British Columbia, Canada, V3K 2Y8

[21] Appl. No.: 737,724

[22] Filed: May 28, 1985

[51] Int. Cl.[4] ..... A01H 5/00

[52] U.S. Cl. ..... Plt./14

[58] Field of Search ..... Plt./14

*Primary Examiner*—Robert E. Bagwill

*Attorney, Agent, or Firm*—Vincent Gioia

[57] ABSTRACT

A new large white hybrid tea rose variety.

1 Drawing Figure

The present invention relates to a new and distinct variety of rose plant of the hybrid tea rose class, which was originated by my crossing as seed parent the rose known as "Blanche Mallerin" (U.S. Plant No. 594) and as pollen parent the rose known as "Pascali" (U.S. Plant No. 2,592). The denomination of this new rose is "Canadian White Star".

Among the novel characteristics possessed by this new variety which distinguish it from its parents and all other varieties of which I am aware are its unusually stable pure white flowers of symmetrical, star-like form borne singly, one to a stem, which retain their coloring upon aging. Flowers are of good exhibition form and are desirable for cutting as well as garden decoration, lasting many days on the plant or after cutting. Asexual reproduction by budding of the new variety as performed in Coquitlam, British Columbia, Canada, shows that the foregoing and other distinguishing characteristics come true to form and are established and transmitted through succeeding propagations.

The new variety differs from its parents in being generally whiter in coloring through final maturity and in bloom size.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "15D" is plate 15D of The Royal Horticultural Society Colour Chart.

Parentage: Seedling.

*Seed parent.*—"Blanche Mallerin".

*Pollen parent.*—"Pascali".

Class: Hybrid Tea.

The following observations are made of specimens grown outdoors in Coquitlam, British Columbia, Canada, during the month of August.

FLOWER

Blooming habit: Recurrent.

A. Bud:

(1) *Size.*—Medium.

(2) *Form.*—Pointed.

(3) *Color.*—As sepals divide, buds are white with greenish cast, becoming pure white as petals unfurl.

(4) *Sepals.*—Longer than bud, two or three of the sepals usually foliated.

(5) *Peduncle.*—Length — average. Aspect — upright. Strength — erect. Color — light green.

B. Bloom:

(1) *Size.*—Average size when fully expanded — about 5½ to 6 inches.

(2) *Borne.*—Singly, one to a stem.

(3) *Form.*—High centered, pointed bud opens with good high center remaining high, petals reflex and quill to points and flower displays sharply defined symmetrical, star-like form.

(4) *Petalage.*—Number of petals under normal conditions — about 45.

(5) *Color.*—As petals unfurl, flower coloring remains snow white, near 15D, and remains stable as flower matures. Flowers remain whiter through full maturity than both seed and pollen parents.

C. Petals:

(1) *Texture.*—Thick.

(2) *Appearance.*—Inside satiny and outside satiny.

(3) *Form.*—Elliptic with notch.

(4) *Arrangement.*—Regularly arranged, shingle-like.

(5) *Petaloids in center.*—Few.

(6) *Persistence.*—Drops off cleanly, 12 to 14 days after opening.

(7) *Fragrance.*—Slight to none.

(8) *Lasting quality.*—Very long lasting quality on plant and as cut flower in temperatures 75°-85° F.

REPRODUCTIVE ORGANS

A. Stamens, filaments and anthers:

*Arrangement and color.*—Regularly arranged around styles.

*Color.*—Filaments near 154C, anthers near 20C.

B. Pollen:

*Color.*—Fresh, near 20C.

C. Styles: Medium length.

D. Stigmas:

*Color.*—Near 45B.

E. Hips: Obovate, ¾-⅞ inch, color near 24B when mature, seeds protrude.

PLANT

A. Form: Upright, compact.

B. Growth: Vigorous.

*Height attained.*—About 5 to 6 feet in second and third year.

C. Foliage: Compound 5 leaflets.

(1) *Size.*—Medium.

(2) *Quantity.*—Abundant.

(3) *Color.*—New foliage: Upper side — near 137B to 137C. Under side — near 183A. Old foliage: Upper side — near 139A. Under side — near to 138B.

(4) *Shape.*—Oval, pointed.

(5) *Texture.*—Upper side is leathery, shiny and under side is dull and only main veins are shiny.

(6) *Edge.*—Serrate.

(7) *Serration.*—Ordinary, deep.

(8) *Leaf stem.*—Color — near to 138A. Under side — near 138C.

(9) *Stipules.*—Parallel, auricle facing outward.

(10) *Resistance to disease.*—Blackspot — average. Mildew — excellent.

D. Wood:

(1) *New wood.*—Color — near 183A. Bark — smooth.

(2) *Old wood.*—Color — near 137C. Bark — smooth.

E. Thorns:

(1) *Thorns.*—Quantity (main stalk) — 5 to 8 per 4 inches. On laterals from stalk — 7 to 10 per 4 inches. Form — slightly curved and hooked. Length — medium. Color — near 183A. Position — irregular.

(2) *Prickles.*—Few to none.

F. Winter hardiness: Very winter hardy.

I claim:

1. A new and distinct variety of rose plant of the hybrid tea rose class, substantially as shown and described, characterized particularly by very well formed, large, snow white flowers of symmetrical, star-like form borne one to a stem on a vigorous mildew-resistant plant and which are long lasting on the plant and as cut flowers.

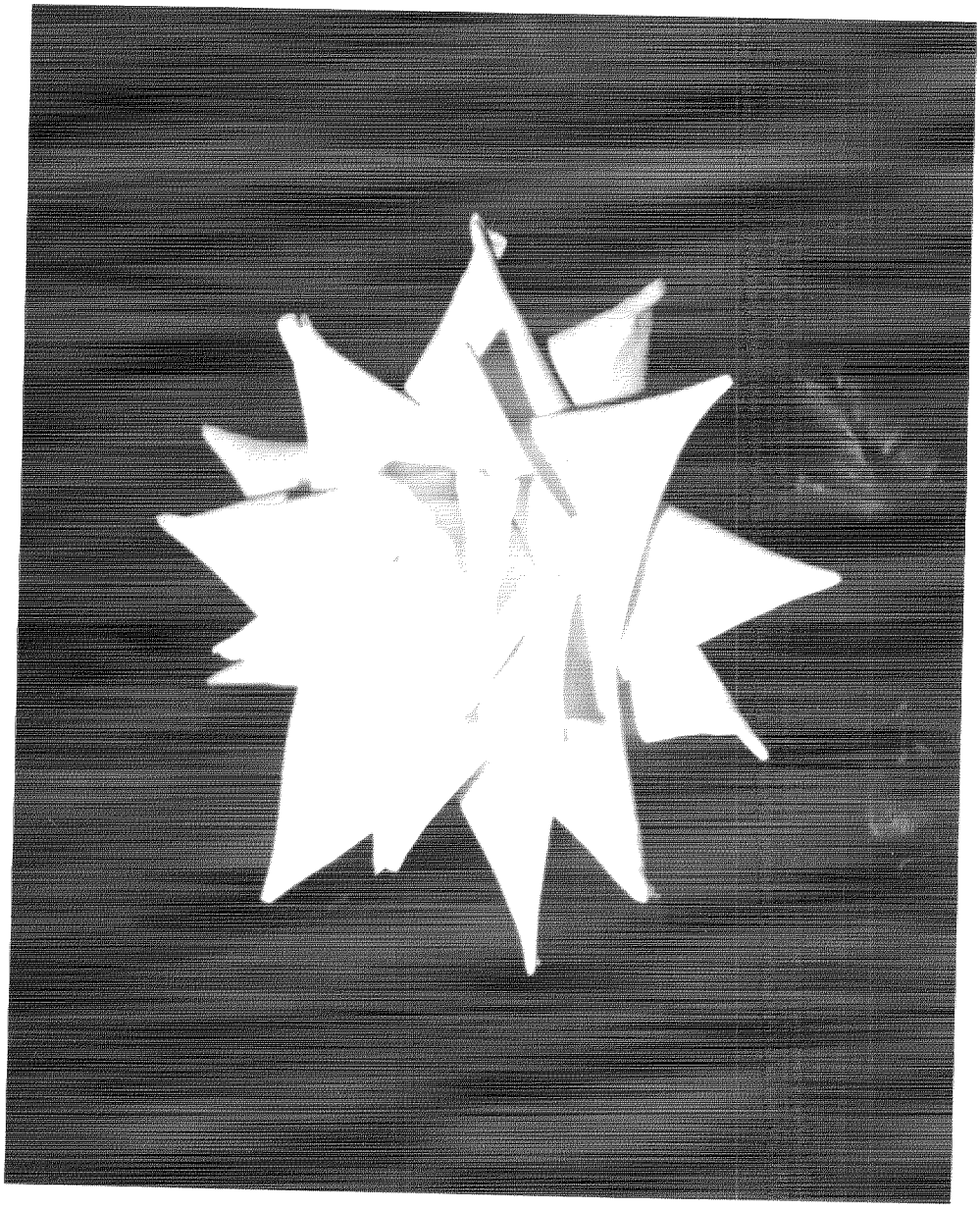

* * * * *